United States Patent
McTaggart et al.

(10) Patent No.: US 9,526,825 B2
(45) Date of Patent: Dec. 27, 2016

(54) MULTIPLE DRUG INFUSION SYSTEM AND METHOD

(71) Applicants: Baxter International Inc., Deerfield, IL (US); Baxter Healthcare S.A., Glattpark (Opfikon) (CH)

(72) Inventors: Natalie McTaggart, Chicago, IL (US); James P. Martucci, Libertyville, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 104 days.

(21) Appl. No.: 14/511,770

(22) Filed: Oct. 10, 2014

(65) Prior Publication Data
US 2015/0025464 A1    Jan. 22, 2015

Related U.S. Application Data

(63) Continuation of application No. 12/730,877, filed on Mar. 24, 2010, now Pat. No. 8,894,631.

(51) Int. Cl.
*A61M 5/14* (2006.01)
*G06F 19/00* (2011.01)
*A61M 5/142* (2006.01)

(52) U.S. Cl.
CPC .......... *A61M 5/1408* (2013.01); *A61M 5/142* (2013.01); *G06F 19/3468* (2013.01); *A61M 2005/14208* (2013.01)

(58) Field of Classification Search
CPC ................ A61M 2005/14208; A61M 5/1408; G06F 19/3468
See application file for complete search history.

(56) References Cited

U.S. PATENT DOCUMENTS

| 4,850,972 A | 7/1989 | Schulman et al. |
| 4,925,444 A | 5/1990 | Orkin et al. |
| 5,153,827 A | 10/1992 | Coutre et al. |
| 5,207,642 A | 5/1993 | Orkin et al. |
| 5,547,470 A | 8/1996 | Johnson et al. |

(Continued)

FOREIGN PATENT DOCUMENTS

| WO | WO02069099 | 9/2002 |
| WO | WO2008106108 | 9/2008 |

OTHER PUBLICATIONS

Japanese Office Action mailed Dec. 18, 2014, corresponding to Japanese Patent Application No. 2013-501448.
International Search Report for for International Application No. PCT/US2011/029761 mailed on Sep. 6, 2011.
Japanese Office Action mailed Sep. 29, 2015, corresponding to Japanese Patent Application No. 2013-501448.

*Primary Examiner* — Kevin C Sirmons
*Assistant Examiner* — Deanna K Hall
(74) *Attorney, Agent, or Firm* — K&L Gates LLP

(57) ABSTRACT

A drug infusion system includes a first infusion pump including a processor and a user interface in operable communication with the processor, and a second infusion pump, wherein the processor of the first infusion pump (i) enables an operator to make a selection using the user interface, the selection specifying a combination of a plurality of drugs to be delivered to a patient using the first and second infusion pumps, and (ii) commands the first infusion pump to deliver one or more drug of the combination to the patient and the second infusion pump to deliver one or more drug of the combination to the patient.

20 Claims, 5 Drawing Sheets

(56) References Cited

U.S. PATENT DOCUMENTS

| | | | |
|---|---|---|---|
| 5,713,856 A | 2/1998 | Eggers et al. | |
| 5,782,805 A | 7/1998 | Meinzer et al. | |
| 5,984,893 A | 11/1999 | Ward | |
| 6,013,057 A | 1/2000 | Danby et al. | |
| RE36,871 E | 9/2000 | Epstein et al. | |
| 6,123,524 A | 9/2000 | Danby et al. | |
| 6,129,887 A | 10/2000 | Barnard et al. | |
| 6,195,887 B1 | 3/2001 | Danby et al. | |
| 6,213,723 B1 | 4/2001 | Danby et al. | |
| 6,213,738 B1 | 4/2001 | Danby et al. | |
| 6,497,680 B1 | 12/2002 | Holst et al. | |
| 6,671,563 B1 | 12/2003 | Engelson et al. | |
| 6,949,079 B1 | 9/2005 | Westberg et al. | |
| 6,985,870 B2 | 1/2006 | Martucci et al. | |
| 7,004,727 B2 | 2/2006 | Kline et al. | |
| 7,029,456 B2 | 4/2006 | Ware et al. | |
| 7,300,418 B2 | 11/2007 | Zaleski | |
| 8,388,598 B2 | 3/2013 | Steinkogler | |
| 2002/0038392 A1 | 3/2002 | De La Huerga | |
| 2002/0169636 A1 | 11/2002 | Eggers et al. | |
| 2004/0176667 A1 | 9/2004 | Mihai et al. | |
| 2004/0193328 A1 | 9/2004 | Zaitsu et al. | |
| 2005/0277912 A1* | 12/2005 | John | A61M 25/0026 604/890.1 |
| 2006/0229557 A1* | 10/2006 | Fathallah | G06F 19/3406 604/131 |
| 2012/0220940 A1 | 8/2012 | Estes et al. | |

\* cited by examiner

MULTIPLE DRUG INFUSION SYSTEM AND METHOD

PRIORITY CLAIM

This application claims priority to and the benefit as a continuation application of U.S. patent application Ser. No. 12/730,877, filed Mar. 24, 2010, entitled "Multiple Drug Infusion System and Method", the entire disclosure of which is hereby incorporated by reference and relied upon.

BACKGROUND

The present disclosure relates generally to medical fluid delivery and in particular to multi-channel infusion pump delivery.

Doctor's routinely order infusion treatments as a specific combination of multiple intravenous ("IV") medications that are to be infused into a patient simultaneously. Common infusion drug combinations include patient preparation for surgery ("pre-op") and patient after surgery ("post-op") combination of antibiotics, anesthetics and/or vasopressors.

The drug combinations are often handled using multi-channel pumps that can deliver different drugs from different sources simultaneously. Multiple channel infusion pumps are known, such as Baxter's multi-channel COLLEAGUE™ Volumetric Infusion Pump made by the assignee of the present disclosure. Previously, each drug of a combination has been entered individually into the pump. Each drug delivery entry presents an opportunity for error in terms of any one of: (i) entering the wrong drug; (ii) entering the dose; and (iii) entering the wrong time in the combination sequence for delivery.

An improved infusion drug combination delivery system and method is needed accordingly.

SUMMARY

The present disclosure has two primary aspects. In one aspect, the present disclosure sets forth a system and method for delivering a protocol or combination of drugs, each drug of the combination or protocol being delivered at a desired time in a sequence to achieve a desired dose. The system and method enables the nurse or technician to select an icon or identifier that represents the desired combination of drugs. The entered drug combination can have preset features and features that are tailored for the patient. The actual drugs of the combination can be preset. The timing and sequence of when the different drugs are delivered can also be preset. The actual amount of the drug or drug dosage, however, can be tailored for the patient. For example, the drugs can be delivered in an amount that is proportional to the patient's weight, e.g., on a per kilogram basis.

In one embodiment, the nurse or technician selects a particular drug combination and enters the patient's weight and/or body surface area ("bsa"). The combination selection sets the particular drugs delivered and the sequence of the drug delivery. The patient's weight or bsa sets the dosage or the amount. In a specific example, the combination can include: (i) a preventative antibiotic A, delivered at a twenty mg/kg (patient weight) dose over one hour; (ii) a preventative antibiotic B, delivered at seven mg/kg dose over 1.5 hours; (iii) a preparatory anesthetic delivered at a twelve mg/kg dose over thirty minutes; and (iv) an anticoagulation drug delivery at a one mg/kg dose over thirty minutes.

If the pump has enough channels to satisfy each of the drugs of the combination, then the nurse or technician programs a single pump. In a second primary aspect of the present disclosure, if the combination requires more channels than any single available pump provides, it is contemplated to use a plurality of pumps and link or multiplex the pumps using a networking tool, such as a wired or wireless network. In one implementation the multiple pumps communicate with a nurse or technician's computer via a wired or wireless network. The inputs necessary to select the drug combination and the patient's weight are stored in software loaded onto the computer. The nurse uses a mouse, curser and keyboard to perform the selections. The selections are then sent over the network to the combination of infusion pumps. The computer can also be used as the combination input device in the situation in which a single pump is handling all drugs in the combination.

In another implementation, the multiplexed pumps are organized in a master/delegate relationship, such that the computer communicates directly with the master infusion pump, or the computer is eliminated and the nurse or patient programs the combination directly at the master pump. In either case, the master pump divides the pumping duties between the two or more infusion pumps according to a predefined protocol. For example, the master computer can fill all of its # of channels with the first # of drugs to be delivered in the combination sequence. Any remaining drugs are then commanded to be delivered by the delegate pump(s). In an alternative embodiment, the master computer splits the different drugs according to functionality, e.g., one of the master and delegate pumps is set to control the delivery of anesthetic drugs, while the other pump is set to control the delivery of drugs used during surgery, e.g., a cardioplegic solution.

It is also contemplated to use a multi-pump system without a network. Here, a master pump communicates with one or more delegate via a wired communication, or via a wireless link that does not require a network to be put in place at the hospital or clinic. Instead, a direct, e.g., infrared, link is established between the master pump and the one or more delegate pump. The nurse can program the master pump and the drugs can be split between the pumps as with the networked multi-pump system.

In either the single or multi-pump systems, it is contemplated to allow the nurse or doctor to modify certain parameters of certain drugs within a range or limit, if desired. It is also contemplated to allow the nurse or operator to enter, along with the patient's weight and/or bsa, a patient identifier. The patient identifier allows access to patient information, such as age, sex, medical and prescription drug history. The patient information can be used to limit the library of drug combinations available for selection and/or to limit how any selected combination can be modified. The patient information may even include a particular drug combination prescribed by the doctor, such that the need for a selection of a drug combination at the machine is eliminated.

It is accordingly an advantage of the present disclosure to provide an improved drug delivery system and method.

It is another advantage of the present disclosure to provide a more efficient system and method for initiating and delivering a combination, protocol or library of drugs.

It is a further advantage of the present disclosure to provide a safer system and method for initiating and delivering a combination of drugs.

It is yet another advantage of the present disclosure to provide a more convenient system and method for initiating and delivering a combination of drugs.

It is yet a further advantage of the present disclosure to multiplex a plurality of pumps for delivering a combination of drugs to a patient.

Additional features and advantages are described herein, and will be apparent from the following Detailed Description and the figures.

DETAILED DESCRIPTION

Figure 1:
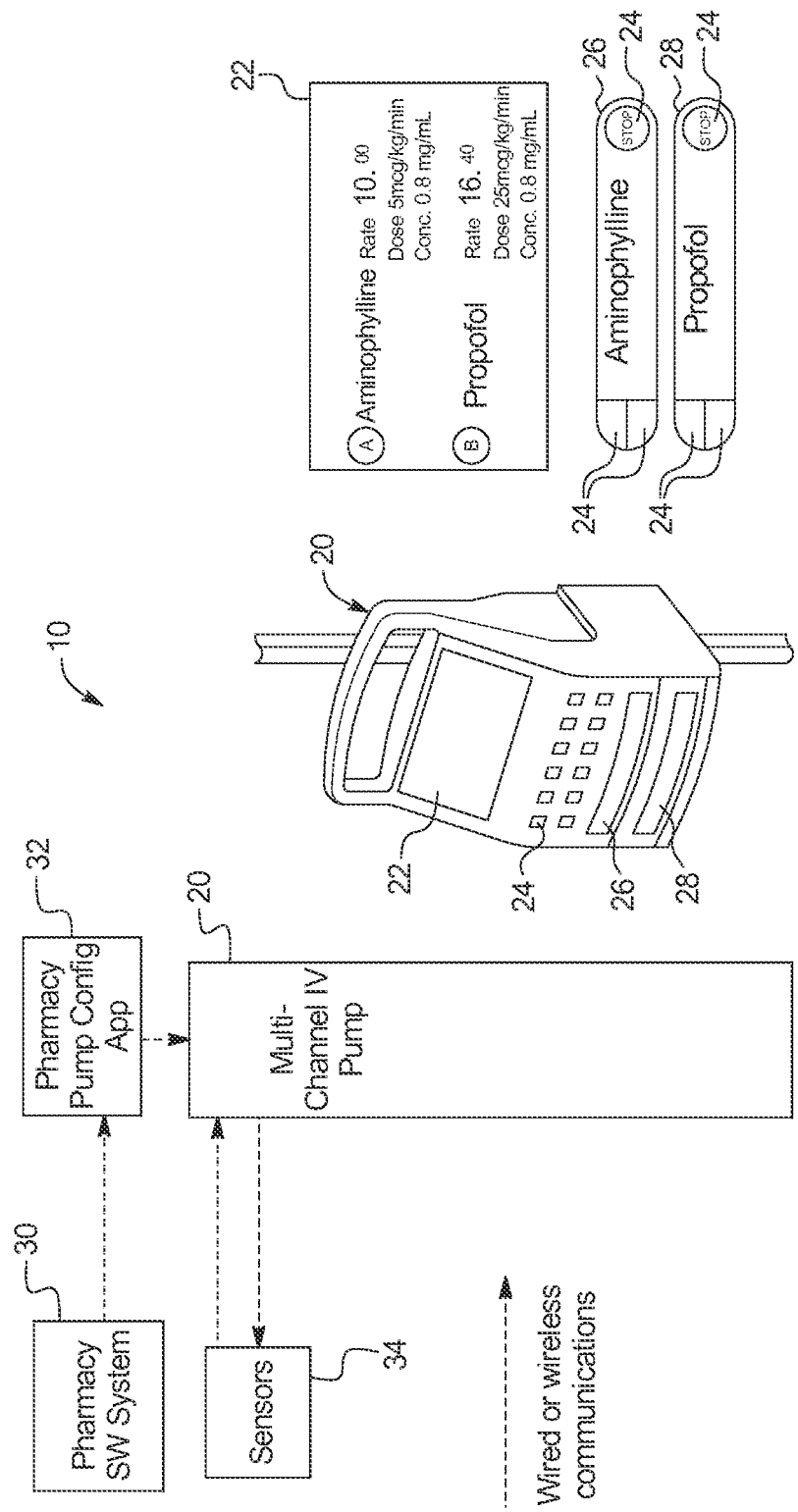
FIG. 1 is a schematic view of one embodiment of a drug combination infusion system of the present disclosure.

Referring now to the drawings and in particular to FIG. 1, one embodiment of the present disclosure is illustrated by system 10. System 10 includes a multi-channel infusion pump 20, which can be configured to interface with a pharmacy server 30 via pharmacy software 32. Pharmacy server 30 and associated software 32 in one embodiment inventory the particular drugs of a combination. Pharmacy software 32 can also be used to configure and store the drug combination protocols. Computerized physician/provider order entry ("CPOE") allows direct entry of a medical order of a protocol by a physician or nurse with the licensure and privileges to do so. Directly entering orders into infusion pump 10 has the benefit of reducing errors by minimizing the ambiguity of hand-written orders. Suitable CPOE systems include those provided by McKesson, G E and Cerner.

In one implementation, the nurse or doctor selects (and confirms) a particular combination of drugs, e.g., from a library stored in physician software 32, after which infusion pump 10 sends the selected combination to pharmacy server 30 via associated software 32. Pharmacy server 30 places an order for the needed drugs, which are then delivered to pump 10. Communication between pump 20 and server 30 can be wired, wireless or some combination thereof. The library of drug combinations in another embodiment is stored in the memory of infusion pump 10.

Pump 20 also interfaces electrically via wired or wireless communication with one or more sensor 34. Sensor 34 can for example be a cardiac monitor, blood pressure sensor, patient weight scale, or a patient chemistry monitor, such as glucometer measuring a patient's glucose level. The patient's weight and/or body surface area ("bsa", bsa is used often for oncology drugs) just prior to infusion of the combination of drugs is important for the present disclosure as discussed herein because the drugs in one embodiment are delivered on a patient weight or per kilogram basis. Other signals, such as blood pressure, are useful during the delivery of the combination of drugs.

Infusion pump 10 includes a display device 22, a plurality of input devices 24, and a plurality of pump channels 26 and 28. Input devices 24 in an embodiment are electromechanical, e.g., membrane switches. Alternatively or additionally, display device 22 operates with a touch screen overlay to input the drug combinations. Also, while pump 10 shows two channels 26 and 28, pump 10 alternatively provides three or more channels.

The blown-up screen 22 of FIG. 1 shows a display of the drugs of a combination entered by the doctor or nurse that are to be delivered to the patient via channels 26 and 28. In the illustrated example, channel 26 delivers Aminophylline at a concentration of 0.8 mg/ml and at a rate of 10.00 ml/hr to achieve an overall dose of five mcg/kg/min. Likewise, channel 28 delivers Propofol at a concentration of 0.8 mg/ml and at a rate of 16.40 ml/hr to achieve an overall dose of twenty-five mcg/kg/min. Both doses are delivered on a per weight or per kilogram basis. The weight and/or bsa of the patient is a variable that is entered into infusion pump 10 at the beginning of treatment either manually via input devices 24 or touch screen or automatically from a weigh scale sensor 34, e.g., wirelessly. One system and process for wirelessly entering patient data, such as weight and blood pressure is set forth in copending U.S. patent application Ser. No. 12/469,371, entitled "System and Method for Automated Data Collection of Twenty-Four Hour Ultrafiltration and Other Patient Parameters Using Wired or Wireless Technology", filed May 20, 2009, the entire contents of which are hereby incorporated expressly by reference and relied upon.

Figure 2:
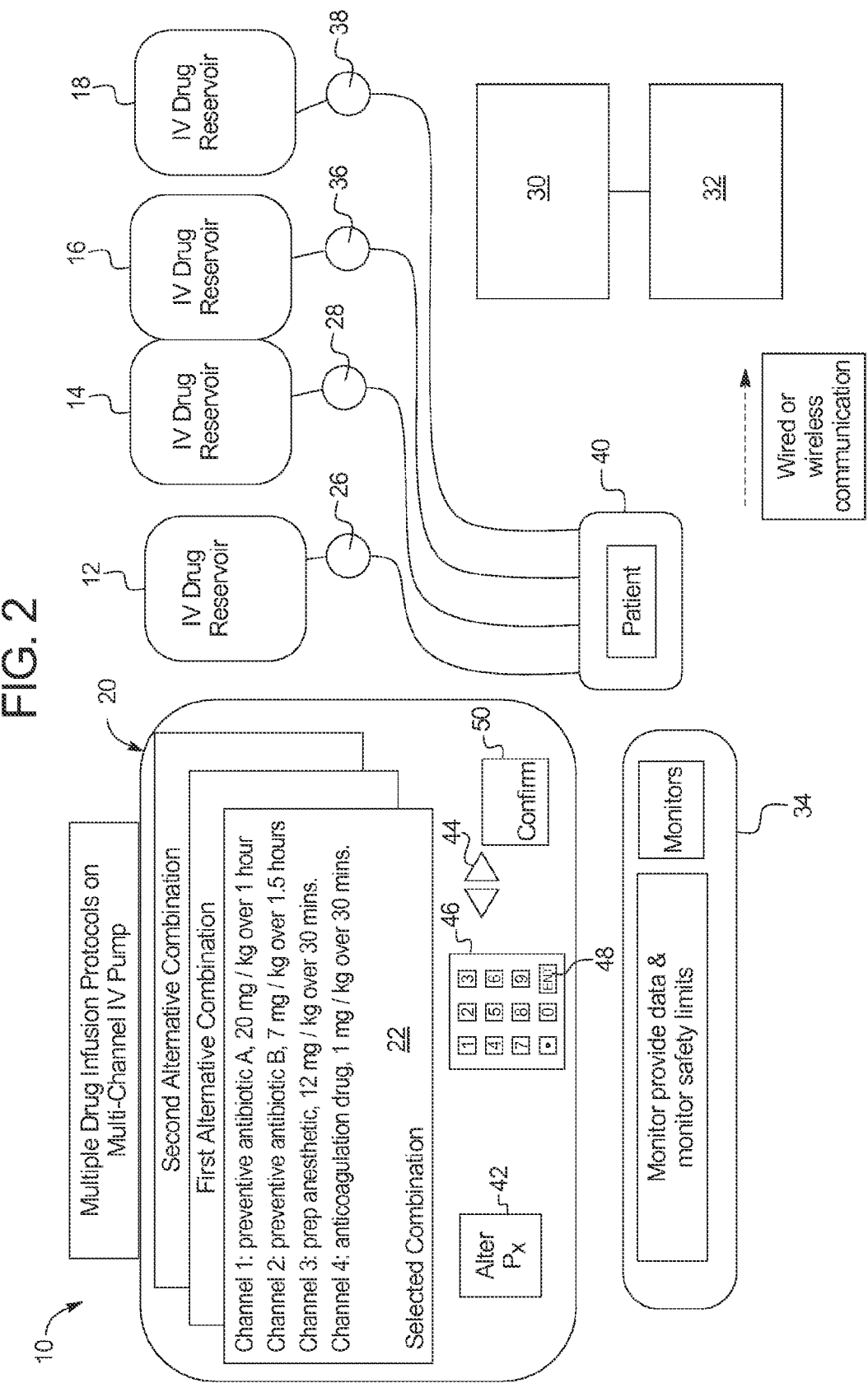
FIG. 2 is a schematic view of another embodiment of a drug combination infusion system of the present disclosure.

FIG. 2 illustrates a four drug combination example of system 10. Here, pump 20 is a four channel pump that pumps from four different drug reservoirs 12, 14, 16 and 18 to patient 40. The nurse or physician here has selected a drug protocol, e.g., from a library accessed via pharmacy software 32, which includes two antibiotics, an anesthetic and an anticoagulation drug. In particular, pump channel 26 pumps a preventative antibiotic A at twenty mg/kg (patient weight) from reservoir 12 over one hour to patient 40. Pump channel 28 pumps a preventative antibiotic B at seven mg/kg from reservoir 14 over 1.5 hours to patient 40. Pump channel 36 pumps a preparatory anesthetic at twelve mg/kg from reservoir 16 over thirty minutes to patient 40. Pump channel 38 pumps an anticoagulation drug at one mg/kg from reservoir 18 over thirty minutes to patient 40. Like with FIG. 1, the pump rates of channels 26, 28, 36 and 38 and drug concentrations are set to achieve the desired dose, which is patient weight dependent. The patient weight and/or bsa can again be entered into infusion pump 20 manually or automatically via a weigh scale 34 in wired or wireless communication with pump 20.

FIG. 2 illustrates another feature of the drug combination delivery systems and methods of the present disclosure, namely, that the combination also specifies the sequence in which the drugs are delivered. Monitor 22 shows the duration of delivery each of the drugs from reservoirs 12, 14, 16 and 18. The durations in one embodiment can all begin at the same starting time, such that anticoagulation drug and the anesthetic drug pumping stops after thirty minutes, antibiotic B is pumped for another thirty minutes and then stopped, after which antibiotic A is pumped for a final thirty minutes. Here, the total drug delivery time is 1.5 hours.

In another embodiment, the drug delivery is sequential, such that, for example, antibiotic A is pumped for the first hour, antibiotic B is pumped for the next 1.5 hours, the anesthetic is pumped for the next thirty minutes, and the anticoagulation drug is pumped for the final thirty minutes. Here, the total drug delivery time is 3.5 hours.

In still a further embodiment, each drug has its own independent delivery start time, which may be the same as or different than the start time of any of the other drugs to be delivered. For all of the above delivery start time scenarios, it is contemplated to store the start times for each of the drugs as part of the overall combination, so that the nurse or doctor does not have to enter such data.

It is therefore contemplated to store with the combination, the drugs involved with the combination, and for each drug its: (i) concentration, (ii) dose, (iii) pump rate, (iv) delivery start time, and (v) delivery duration. Alternatively, pump rate can be calculated knowing concentration and dose. The nurse or doctor then only has to enter the drug combination selection and the patient's weight (or command that the weight be sent via a weigh scale).

System 10 in one embodiment allows the nurse or doctor to alter certain settings of the combination. For example, it may occur that the prescribed concentration of one of the drugs is not available, but that the drug in another concentration is available. The nurse or doctor can select the alter Px button 42, which causes monitor 22 to highlight the first alterable parameter of the prescription shown on screen 22. The nurse or doctor scrolls through the alterable parameters, e.g., via arrow keys 44, until the desired parameter to be altered is highlighted. The nurse or doctor then uses keyboard 46 to digitally enter a new value for the parameter (or alternatively uses arrow keys to raise or lower the current value by a preset increment) and selects the enter button 48. In an embodiment, all selections made by the nurse or operator require a confirm input using confirm button 50 for infusion pump 20 to actually implement the selection or modification.

Any modifications to the prescription can be subject to a range or a limit. If the nurse or doctor attempts to enter a value for a parameter that is out of range or out of limit, infusion pump 20 sends an error message and does not allow the attempted value to be confirmed.

Any modifications to the prescription, and indeed the selection of the combination itself, are in one embodiment limited by the patient's physical and chemical condition. Here, system 10 can limit the range of parameter adjustment or the available drug combinations based on patient age, sex, ailment, medical history, prescription drugs taken or other physical characteristics.

Figure 3:
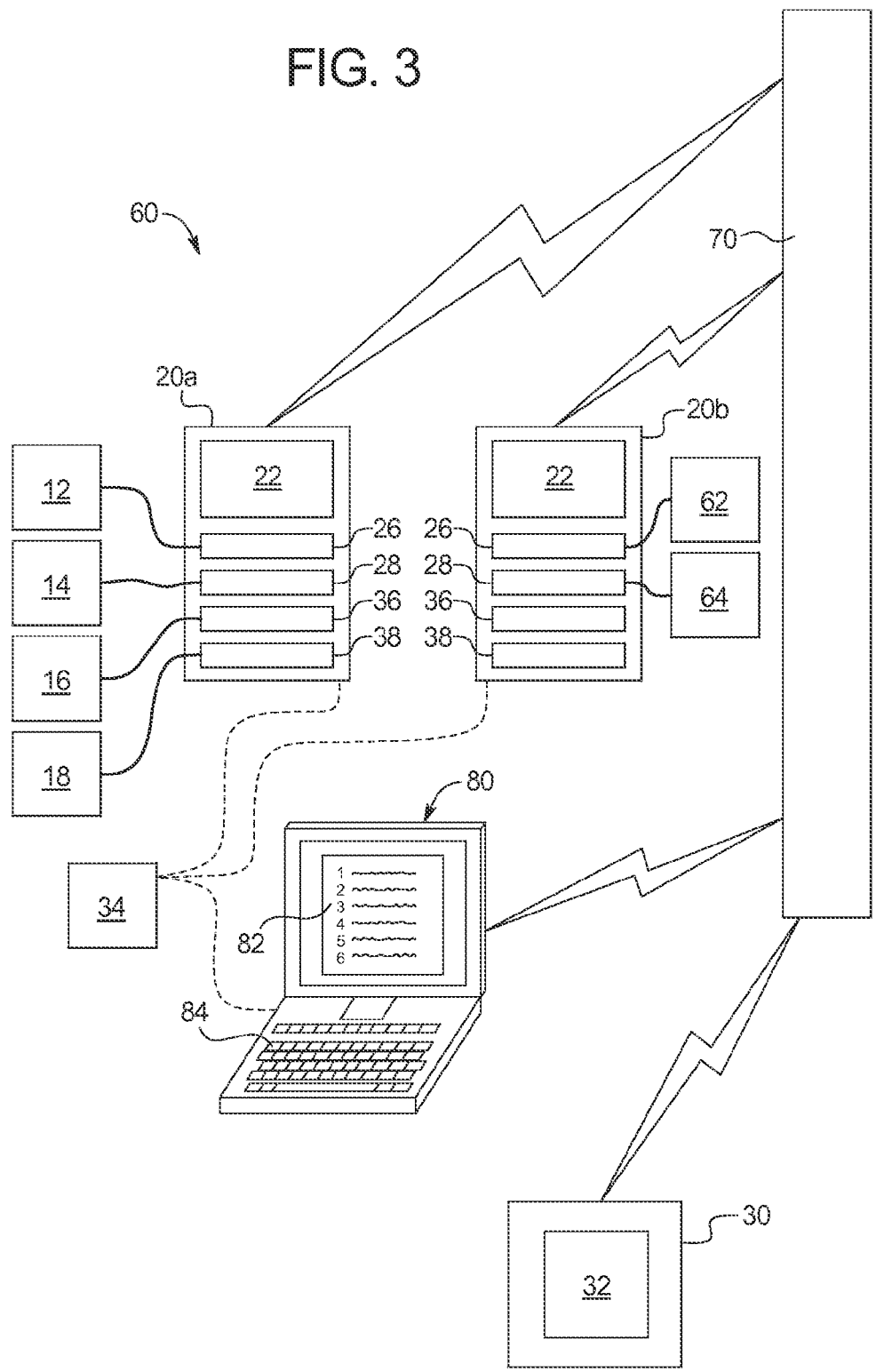
FIG. 3 is a schematic view of one embodiment of a networked multiple infusion pump drug combination infusion system of the present disclosure.

Referring now to FIG. 3, system 60 illustrates one embodiment of a multiple infusion pump drug combination delivery system of the present disclosure. It may be that the selected combination requires more drugs than any single pump has channels. System 60 addresses this situation via the use of multiple infusion pumps 20a and 20b. The six drug combination of FIG. 3, pulling six different drugs from reservoirs 12, 14, 16, 18, 62 and 64, can use two four-channel pumps as shown or three two-channel pumps based on availability. That is, system 60 can multiplex as many infusion pumps 20 (referring collectively to pumps 20a, 20b, 20n . . . ) as necessary. System 60 includes a network 70 (which can also be used with system 10 as discussed above), which interfaces with pumps 20a and 20b, pharmacy system 30 storing software 32 and a front end computer 80. Sensors 34 in various implementations communicate with: (i) computer 80 only; (ii) computer 80 and master pump 20a only; (iii) computer 80 and each pump 20a, 20b, 20n . . . as needed; (iv) master pump 20a only (e.g., if computer 8 not provided); or (v) each pump 20a, 20b, 20n . . . as needed (e.g., if computer 80 not provided). Network 70 can be wired (e.g., serial or Universal Serial Bus ("USB") linked) or wireless (e.g., 802.11, Zigbee™, or Bluetooth™). Computer 80 can be used with either system 10 or system 60 as the input device that the nurse or doctor uses in place of infusion pump 10.

Computer 80 includes a display 82 showing the selected combination to the user. FIG. 3 shows drugs one to six. Computer 80 also includes buttons 82 that allow the nurse or doctor to enter information into system 60. The drug combinations can be stored at pharmacy server 30 and loaded onto computer 80 when needed. Once the selected drug combination is entered, computer 80 sends the selection to network 70. Network 70 then uses each channel 26, 28, 36 and 38 of a first pump 20a for four drugs of the selected combination, namely, drugs from reservoirs 12, 14, 16 and 18 in the illustrated embodiment. The four drugs can be the first four drugs delivered in the sequence of the combination or be grouped by drug type or purpose. Network 70 uses as many channels 26, 28, 36 and 38 of the second pump 20b as necessary to complete the combination, here, channels 26 and 28 to pump from reservoirs 62 and 64.

In an embodiment, computer 80 designates which pump 20a and 20b delivers which drug from which container 12, 14, 16, 18, 62 and 64. Again, selection can be made based on sequence of when the different drugs are delivered or can bunch the drugs according to type, e.g., one pump 20a or 20b pumps antibiotics and drugs needed for a particular surgery, e.g., an anticoagulation drug for open heart surgery, while the other pump 20a or 20b pumps different anesthetics. For example, it may be that the anesthetic drug pump needs to be more closely monitored and adjusted during surgery, such that it is desirable to locate that pump near the anesthesiologist, while the other pump can be kept out of the way of the surgery. The participant pumps when chosen by computer 80 can sound an alert or otherwise distinguish themselves as being participants in the drug combination delivery. Computer 80 can also provide information as to which pumps have been selected and perhaps the location of each pump, especially if the pumps are in different rooms or areas of the hospital.

The selection of which pump pumps which drug can be done manually at computer 80, be performed automatically according to a protocol in software on computer 80, or be performed automatically according to a protocol in software on computer 80 but allowing for a manual override. The selection is sent from computer 80 over network 70 to pumps 20a and 20b, which display the information to the nurse or doctor, who then (i) confirms or (ii) modifies and confirms the drug delivery combination for each pump. In an embodiment, computer 80 keeps a master clock or timer for each pump 20a, 20b, 20n . . . used in the combination, so that the drug delivery for each pump can be coordinated with each other pump used in the overall drug combination. In an embodiment, to avoid confusion, the entire drug combination is shown on each participating pump 20a, 20b, 20n . . . , and wherein the particular drugs of the combination that are being pumped by each individual pump 20a, 20b, 20n . . . are highlighted on that pump. In that way, a person viewing any of the pumps participating in the combination delivery knows that (i) other pumps are required and are potentially in operation delivering their drugs (ii) all of the drugs of the combination and their sequence of delivery.

In an alternative embodiment, computer 80 is not used and instead one of the pumps 20a, 20b, 20n . . . is set as a master pump, which oversees the other pumps used in the combination. Here, it is contemplated that any pump can be the master pump and that when the nurse selects a combination at any pump that has less channels than are needed for the drug combination, the pump (i) can look to see if there is a pump in the room or nearby that has enough channels to satisfy the remainder of the combination; and (ii) enlists the help of a nearby pump if an additional one or more channel is needed. That enlisted one or more pump then becomes subordinate to the original pump. Communication between pumps 20a, 20b, 20n . . . is via network 70 as illustrated.

The one or more enlisted pump can sound an alert or otherwise distinguish itself as the enlisted pump. The master pump can also provide information as to which pump(s) has been enlisted and perhaps the location of the pump, especially if in a different room or area of the hospital. The master and enlisted pumps in one embodiment each show the entire drug combination, and highlight each of the particular drugs of the combination that are being pumped by that pump. Again, that way a person viewing any of the pumps participating in the combination delivery knows that (i) other pumps are required and are potentially in operation delivering their drugs (ii) all of the drugs of the combination and their sequence. The method of determining which pump 20a, 20b, 20n . . . pumps which drug is done as described above for the embodiment using computer 80.

Figure 4:
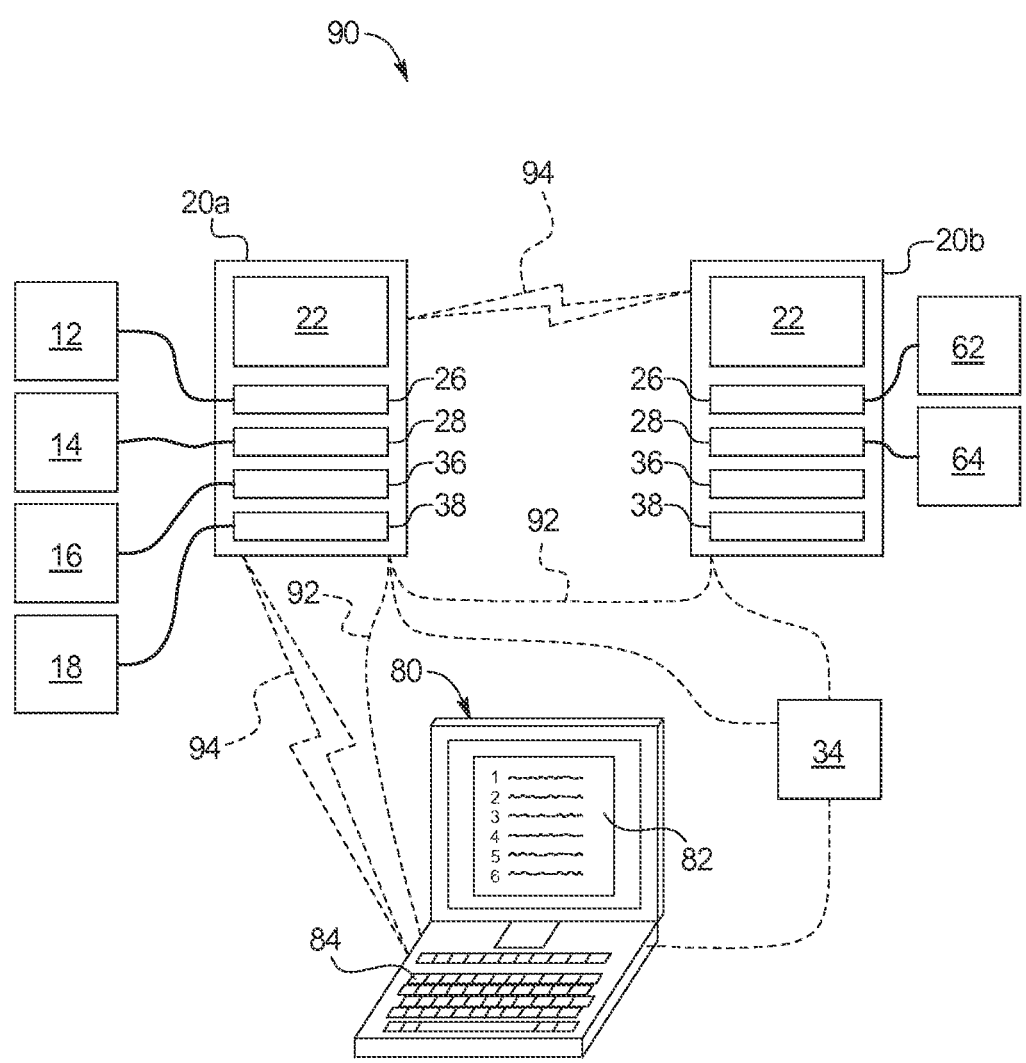
FIG. 4 is a schematic view of one embodiment of a non-networked multiple infusion pump drug combination infusion system of the present disclosure.

Referring now to FIG. 4, system 90 illustrates an alternative, non-networked multi-pump system embodiment. Hospitals or clinical centers may have the requisite network 70 of FIG. 3 in place, or may allow one to be installed. On the other hand, the hospital or clinic may not have network 70 in place and may not want to incur the complication and expense of adding such a network. System 90 enables the methodology described herein to be implemented without a network, such as network 70.

System 90 may operate with the doctor or nurse operating computer 80, which communicates via master pump 20a, which in turn commands one or more delegate pump, 20b, 20c, 20n . . . . Alternatively, computer 80 is not used and the doctor or nurse programs the system at master computer 20a, which in turn commands one or more delegate pump, 20b, 20c, 20n . . . . Any of the above communication may be done alternatively via wire 92 or via a wireless link 94 (thus shown dashed), such as Bluetooth™, Zigbee™, or other protocol, e.g., one based on IEEE 802.

One primary difference between system 90 and system 60 is that the pharmacy system 30 storing software 32 accessible in previous embodiments over the network is not available with system 90. The drug combination library is therefore stored semi-permanently at computer 80 or pump 20a, 20b, etc. Sensors 34 in various implementations, like above, communicate with: (i) computer 80 only; (ii) computer 80 and master pump 20a only; (iii) computer 80 and each pump 20a, 20b, 20n . . . as needed; (iv) master pump 20a only (e.g., if computer 8 not provided); or (v) each pump 20a, 20b, 20n . . . as needed (e.g., if computer 80 not provided).

In an embodiment, as described above with system 60, computer 80 in system 90 designates which pump 20a and 20b delivers which drug from which container 12, 14, 16, 18, 62 and 64. The selection of which pump pumps which drug can be done manually at computer 80, be performed automatically according to a protocol in software on computer 80, or be performed automatically according to a protocol in software on computer 80 but allowing for a manual override.

In an alternative embodiment, computer 80 is not used and instead system 90 sets one of the pumps 20a, 20b, 20n . . . as a master pump, which oversees the other pumps used in the combination. Here again, it is contemplated that any pump can be the master pump and that when the nurse selects a combination at any pump that has less channels than are needed for the drug combination, the pump (i) can look to see if there is a pump in the room or nearby that has enough channels to satisfy the remainder of the combination; and (ii) enlists the help of a nearby pump if an additional one or more channel is needed. The one or more enlisted pump can sound an alert or otherwise distinguish itself as the enlisted pump.

Whether or not system 10, 60 or 90 is used, it is contemplated to equip pump 20 or participating pumps 20a, 20b, 20n . . . with a reader (e.g., barcode or radio frequency ("RF") reader) that reads a label (e.g., barcode label or radio frequency identification ("RFID") tag) located on drug reservoirs 12, 14, 16, 18, 62 and 64 to ensure that the correct pump is pumping the correct drug. One suitable pump having built-in scanning capability is set forth in copending patent application Ser. No. 10/855,872, entitled "Identification Information Recognition System For a Medical Device", filed May 27, 2004, the entire contents of which are incorporated herein by reference and relied upon.

Figure 5:
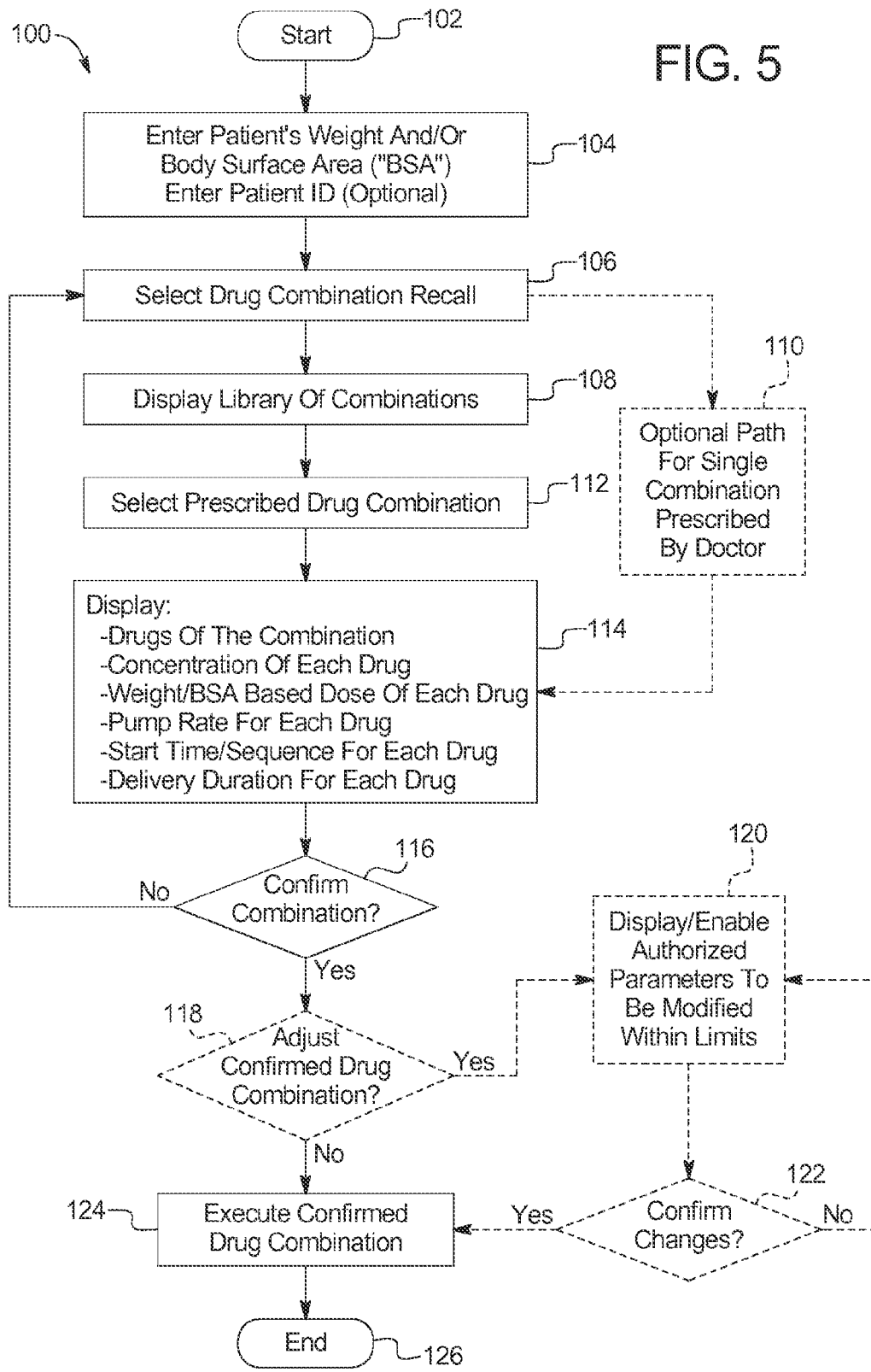
FIG. 5 is a schematic flowchart of one embodiment of a drug combination delivery infusion method of the present disclosure, which is applicable to the single and multiple infusion pump systems.

Referring now to FIG. 5, method 100 illustrates (and summarizes) suitable methods of operation for any of systems 10, 60 or 90 described above. At oval 102 method 100 begins. The nurse or doctor enters the patient's weight and/or bsa or has the patient stand on a scale that sends a signal (e.g., over wired or wireless network 70) inputting the patient's weight to infusion pump 20 or computer 80, as seen at block 104.

Block 104 also indicates that the nurse or doctor optionally enters a patient identification, such as the patient's name, social security number, birth date or some combination thereof, such that system 10, 60 or 90 can access information stored for the patient, such as age, sex, medical history, prescription drugs taken and current ailment or needed surgical procedure. At block 106, the nurse or doctor initiates the drug combination recall at pump 20 or computer 80. In one embodiment, pump 20 or computer 80 lists a library of possible drug combinations for the patient, from which the nurse chooses a single desired drug combination for delivery, as seen at block 108. The library can be tailored to or limited by the patient information, e.g., certain combinations may not be available for children or for patients taking certain prescription drugs.

At block 112, the nurse or doctor selects the patient's prescribed drug combination from the library of possible drug combinations. Alternative block 110 (dashed to indicate alternative) shows another embodiment in which a doctor-prescribed drug combination is provided upon entering the patient identification information, such that the decision at the pump indicated by block 112 is eliminated. In either case, at block 114, pump 20 or multiple pumps 20a, 20b, 20n . . . display drug combination information, such as: (i) drugs of the combination; (ii) concentration of each drug; (iii) a weight and/or bsa based dose of each drug (which in combination with the patient's weight and/or bsa enables dose to be determined); (iv) pump rate for each drug; (v) start time/sequence for each drug; and (vi) delivery duration for each drug. Again, if multiple pumps 20a, 20b, 20n . . . are used to deliver the entire combination, each pump shows the entire drug combination and highlights the particular drug or drugs that the pump is to deliver in one embodiment. Some of the displayed information can be hidden as needed so as not to clutter pump display device 22 or computer display device 82, for example, until the nurse or doctor selects a particular drug, after which all information concerning that drug is displayed.

At diamond 116, the nurse or doctor confirms or rejects the combination displayed at block 114. If the doctor or nurse mistakenly selects the wrong drug combination at block 112, systems 10, 60 and 90 enable the doctor or nurse to back out of the wrongly selected combination and reselect the drug combination recall at block 106, starting anew the sequence between block 106 and diamond 116.

If the nurse or doctor confirms the selected drug combination at diamond 116, system 10, 60 or 90 employing method 100 optionally enters a drug combination adjustment sequence as seen at diamond 118 (dashed to indicate optional). As discussed above, systems 10, 60 and 90 may allow for certain parameters of certain drugs of the combination to be modified, e.g., within a range or limit Any one or more of the parameters, drugs and ranges/limits available for modification may be subject to or affected by the patient information accessed optionally, at block 104.

If the nurse or doctor does wish to modify the combination at diamond 118, the nurse or doctor makes the appropriate selection indicating so at pump 20 or computer 80 and enters the changes into pump 20 or computer 80 as indicated at block 120. If the nurse or doctor decides against a change that has been inputted into pump 20 or computer 80, or wishes to modify the change, this can be done as indicated by diamond 122, in which case the nurse or doctor is returned to modification entry block 120. If the nurse or doctor confirms the changes at diamond 122, or if a change is not desired as indicated at diamond 118 (or is not available if diamond 118, block 120 and diamond 122 are not provided), system 10, 60 or 90 executes the confirmed (and potentially modified) drug combination as indicated by block 124. Method 100 is thus completed as indicated by oval 186.

Aspects of the subject matter described herein may be useful alone or in combination one or more other aspect described herein. Without limiting the foregoing description, in a first aspect of the present disclosure, a medical drug infusion system includes: an infusion pump; an input device; and a processor, the input device and processor configured to allow an operator to make a selection that specifies a preprogrammed combination of a plurality of drugs to be delivered to a patient, the input device and processor further configured to allow the operator to enter (i) the identification, (ii) weight and/or (iii) body surface area ("bsa") of the patient, at least one of the plurality of drugs delivered based on the entered weight and/or bsa of the patient.

In accordance with a second aspect of the present disclosure, which may be used in combination with the first aspect, each of the drugs is delivered based on the entered weight and/or bsa of the patient.

In accordance with a third aspect of the present disclosure, which may be used in combination with any one or more of the preceding aspects, the combination of drugs includes a sequence in which the plurality of drugs is delivered.

In accordance with a fourth aspect of the present disclosure, which may be used in combination with any one or more of the preceding aspects, at least one of a rate, a dose and a concentration is specified for at least one of the drugs.

In accordance with a fifth aspect of the present disclosure, which may be used in combination with the fourth aspect, the dose is based on the entered weight and/or bsa of the patient.

In accordance with a sixth aspect of the present disclosure, which may be used in combination with the fourth aspect, the rate is specified to achieve the specified dose.

In accordance with a seventh aspect of the present disclosure, which may be used in combination with the fourth aspect, the concentration is predetermined.

In accordance with an eighth aspect of the present disclosure, which may be used in combination with any one or more of the preceding aspects, the plurality of drugs are of a type selected from the group consisting of: (i) an antibiotic, (ii) an anesthetic, (iii) an anticoagulant, and (iv) a drug to manage hypertension.

In accordance with an ninth aspect of the present disclosure, which may be used in combination with any one or more of the preceding aspects, the infusion pump is a multi-channel pump, each of the plurality of drugs delivered via one of the channels of the multi-channel pump.

In accordance with an tenth aspect of the present disclosure, which may be used in combination with any one or more of the preceding aspects, at least one of the input device and the processor is integrated with the infusion pump.

In accordance with an eleventh aspect of the present disclosure, which may be used in combination with any one or more of the preceding aspects, at least one of the input device and the processor are located on a remote computer in communication with the infusion pump.

In accordance with a twelfth aspect of the present disclosure, which may be used in combination with any one or more of the preceding aspects, the selection is made from a library of selections, each selection associated with a different combination of drugs.

In accordance with a thirteenth aspect of the present disclosure, which may be used in combination with the twelfth aspect, the system includes a display device that displays the library of selections to the operator.

In accordance with a fourteenth aspect of the present disclosure, which may be used in combination with any one or more of the preceding aspects, the system includes (i) a display device that displays the combination of drugs to the operation and (ii) a confirm function requiring the operator to confirm that the displayed combination of drugs is correct before delivery to the patient.

In accordance with a fifteenth aspect of the present disclosure, which may be used in combination with any one or more of the preceding aspects, the system includes a mechanism that verifies a drug of a supply for operation with the infusion pump is one of the selected combination of drugs.

In accordance with a sixteenth aspect of the present disclosure, which may be used in combination with any one or more of the preceding aspects, a drug infusion system includes: a first infusion pump; a second infusion pump; an input device; and a processor, the input device and the processor configured to allow an operator to make a selection that specifies a combination of a plurality of drugs to be delivered to the patient using the first and second infusion pumps.

In accordance with a seventeenth aspect of the present disclosure, which may be used with any one or more of the preceding aspects in combination with aspect 16, the first infusion pump is a master infusion pump and the second infusion pump is a delegate infusion pump, the first pump determining which one or more drug of the combination is to be pumped by the second pump.

In accordance with an eighteenth aspect of the present disclosure, which may be used with any one or more of the preceding aspects in combination with aspect 16, the drug infusion system assigns each of a plurality of channels of the first infusion pump to a plurality of the drugs of the combination and employs the second infusion pump if one or more drug of the combination has not been assigned.

In accordance with a nineteenth aspect of the present disclosure, which may be used with any one or more of the preceding aspects in combination with aspect 16, the drug infusion system designates different drugs of the combination to the first infusion pump or the second infusion pump according to at least one of (i) a sequence of delivery of the plurality of drugs; and (ii) type of each of the plurality of drugs.

In accordance with a twentieth aspect of the present disclosure, which may be used in combination with any one or more of the preceding aspects, an infusion pump method includes: displaying a library of drug combination selections; enabling an operator to select one of the drug combination selections for a patient; displaying the drugs of a selected one of the drug combination selections to the operator; receiving a confirm input from the operator confirming the displayed drugs of the selected drug combination selection; and delivering the displayed drugs to the patient.

In accordance with a twenty-first aspect of the present disclosure, which may be used with any one or more of the preceding aspects in combination with aspect 20, the infusion pump method includes delivering the displayed drugs to the patient based on a weight and/or body surface area of the patient.

In accordance with a twenty-second aspect of the present disclosure, any of the structure and functionality illustrated and described in connection with FIG. 1 may be used in combination with any one or more of the preceding aspects.

In accordance with a twenty-third aspect of the present disclosure, any of the structure and functionality illustrated and described in connection with FIG. 2 may be used in combination with any one or more of the preceding aspects.

In accordance with a twenty-fourth aspect of the present disclosure, any of the structure and functionality illustrated and described in connection with FIG. 3 may be used in combination with any one or more of the preceding aspects.

In accordance with a twenty-fifth aspect of the present disclosure, any of the structure and functionality illustrated and described in connection with FIG. 4 may be used in combination with any one or more of the preceding aspects.

In accordance with a twenty-sixth aspect of the present disclosure, any of the structure and functionality illustrated and described in connection with FIG. 5 may be used in combination with any one or more of the preceding aspects.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A drug infusion system comprising:
a first infusion pump including a first processor and a first user interface in operable communication with the first processor; and
a second infusion pump including a second processor and a second user interface in operable communication with the second processor,
wherein either one of the first infusion pump or the second infusion pump can be designated as a master infusion pump such that the respective first or second processor of the master infusion pump (i) enables an operator to make a selection using the respective first or second user interface, the selection specifying a combination of a plurality of drugs to be delivered to a patient using the first and second infusion pumps, and (ii) commands the first infusion pump to deliver one or more drug of the combination to the patient and the second infusion pump to deliver one or more drug of the combination to the patient.

2. The drug infusion system of claim 1, wherein each of the first and second user interfaces enables the operator to enter at least one of (a) an identification, (b) a weight or (iii) a body surface area of the patient.

3. The drug infusion system of claim 2, wherein a dose of at least one of the drugs of the combination is determined based upon at least one of (a), (b) or (c).

4. The drug infusion system of claim 2, wherein at least one of a rate or a concentration of at least one of the drugs of the combination is determined based upon at least one of (a), (b) or (c).

5. The drug infusion system of claim 1, wherein the respective first or second processor of the master infusion pump determines which one or more drug of the combination is to be delivered by the other of the first or second infusion pumps according to at least one of (a) a sequence of a delivery of the plurality of drugs or (b) a type of each of the plurality of drugs.

6. The drug infusion system of claim 1, wherein the master infusion pump includes a number of drug infusion channels, and wherein the respective first or second processor of the master infusion pump commands the other of the first or second infusion pumps to deliver its one or more drug of the combination if the number of the plurality of drugs is greater than the number of drug infusion channels.

7. The drug infusion system of claim 1, wherein the respective first or second processor of the master infusion pump commands the other of the first or second infusion pumps to deliver its one or more drug of the combination after the master infusion pump delivers its one or more drug of the combination.

8. The drug infusion system of claim 1, wherein the selection of the drug combination is made from a library of different drug combinations.

9. The drug infusion system of claim 8, wherein the respective first or second user interface of the master infusion pump displays the library of different drug combinations to the operator.

10. The drug infusion system of claim 1, wherein at least one of the respective first or second processor and the respective first or second user interface is integrated with the master infusion pump.

11. A drug infusion system comprising:
a first infusion pump including a first processor and a first user interface in operable communication with the first processor; and
a second infusion pump including a second processor and a second user interface in operable communication with the second processor,
wherein either one of the first infusion pump or the second infusion pump can be designated as a master infusion pump such that the respective first or second processor of the master infusion pump (i) enables an operator to make a selection using the respective first or second user interface that specifies a combination of a plurality of drugs to be delivered to a patient using the first and second infusion pumps, (ii) determines a sequence of delivery of the plurality of drugs, and (iii) commands the first and second infusion pumps to each deliver at least one drug of the sequence.

12. The drug infusion system of claim 11, wherein the respective first or second processor of the master infusion pump determines the sequence of delivery based on a type of each of the plurality of drugs.

13. The drug infusion system of claim 11, wherein the respective first or second processor of the master infusion pump determines a timed delivery start for at least one drug of the plurality of drugs of the combination.

14. The drug infusion system of claim 13, wherein the respective first or second processor commands the other of the first or second infusion pumps to deliver its at least one drug at the timed delivery start.

15. The drug infusion system of claim 11, wherein the other of the first or second infusion pumps delivers its at least one drug after the master infusion pump delivers its at least one drug according to the sequence of delivery.

16. A drug infusion system comprising:
a first infusion pump including a first processor and a first user interface in operable communication with the first processor; and
a second infusion pump including a second processor and a second user interface in operable communication with the second processor,
wherein either one of the first infusion pump or the second infusion pump can be designated as a master infusion pump such that the respective first or second processor of the master infusion pump (i) enables an operator to make a selection using the respective first or second user interface that specifies at least one drug to be delivered to a patient, (ii) commands the first infusion pump to deliver the at least one drug to the patient, and (iii) commands the second infusion pump to deliver the at least one drug to the patient.

17. The drug infusion system of claim 16, wherein the selection specifies a combination of a plurality of drugs delivered to the patient, the respective first or second processor commanding the other of the first or second infusion pumps to deliver a different drug of the combination than the master infusion pump.

18. The drug infusion system of claim 16, wherein at least one of the respective first or second processor and the respective first or second user interface is integrated with the master infusion pump.

19. The drug infusion system of claim 16, wherein the respective first or second user interface of the master infusion pump provides information regarding a location of the other of the first or second infusion pumps.

20. The drug infusion system of claim 16, wherein the other of the first or second infusion pumps issues an alert when found by the master infusion pump.

* * * * *